United States Patent [19]

New et al.

[11] Patent Number: 5,206,365
[45] Date of Patent: Apr. 27, 1993

[54] PSYCHOTROPIC HETEROBICYCLOALKYLPIPERAZINE DERIVATIVES

[76] Inventors: James S. New, 168 Bradley Corners, Madison, Conn. 06483; William L. Christopher, 103 Charlesberry La., Chapel Hill, N.C. 27514

[21] Appl. No.: 844,336

[22] Filed: Mar. 2, 1992

Related U.S. Application Data

[62] Division of Ser. No. 630,672, Dec. 20, 1990, Pat. No. 5,116,970, which is a division of Ser. No. 157,016, Feb. 18, 1988, Pat. No. 5,001,130.

[51] Int. Cl.$^5$ .............. C07D 491/048; C07D 495/04; C07D 519/00
[52] U.S. Cl. ........................... 544/278; 544/235; 544/295
[58] Field of Search ........................... 544/278

[56] References Cited

U.S. PATENT DOCUMENTS

| 4,670,560 | 6/1987 | Press et al. | 544/278 |
| 4,703,120 | 10/1987 | Press et al. | 544/278 |
| 4,835,157 | 5/1989 | Press et al. | 544/278 |
| 5,001,130 | 3/1991 | New et al. | 544/278 |

FOREIGN PATENT DOCUMENTS 329168 8/1989 European Pat. Off. ............ 544/295

Primary Examiner—Nicholas S. Rizzo
Assistant Examiner—E. Bernhardt
Attorney, Agent, or Firm—Richard P. Ryan

[57] ABSTRACT

A series of psychotropic heterobicycloalkylpiperazine derivatives having the structure

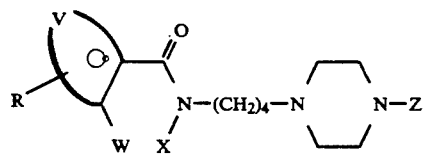

wherein V is a 3- or 4-membered unsaturated chain, containing all carbon atoms when 4-membered, or when a 3-membered chain, V contains an oxygen or sulfur atom as one of the members; R is H or $C_{1-4}$ alkyl; W is CH, N, $CH_2$, or a chemical bond; X is CH, N, $SO_2$, or CO, with the proviso that both W and X cannot simultaneously be N; and Z is a heteroaromatic ring system. These compounds are useful antipsychotic and/or anxiolytic agents.

5 Claims, No Drawings

PSYCHOTROPIC HETEROBICYCLOALKYLPIPERAZINE DERIVATIVES

CROSS-REFERENCE TO RELATED APPLICATIONS

This is a divisional application of Ser. No. 07/630,672 filed Dec. 20, 1990 and issued May 26, 1992 as U.S. Pat. No. 5,116,970. Ser. No. 07/630,672 was itself a divisional application of Ser. No. 07/157,016 filed Feb. 18, 1988, now U.S. Pat. No. 5,001,130.

BACKGROUND OF THE INVENTION

This invention generally pertains to heterocyclic carbon compounds having drug and bio-affecting properties and to their preparation and use. In particular, the invention is concerned with 1,4-disubstituted piperazine derivatives wherein the 1- substituent is a bicyclic heterocycle containing an incorporated amide or imide moiety whose nitrogen atom is the point of attachment via a butylene chain; and the 4- substituent is a heterocycle comprising pyrimidine, 1,2-benzisothiazole, thieno[3,2-c]pyridine, or furo[3,2-c]pyridine.

Related art may be viewed in terms of the following general structural formula 1

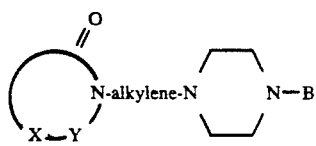

Compounds of general structure 1 wherein X is $C_{2-3}$ alkanediyl and Y is carbonyl, so that a cyclic imide such as glutarimide, succinimide, phthalimide, and the like is formed, have been disclosed and claimed in the following representative patent references.

A. Wu, et al., in U.S. Pat. No. 3,717,634; Temple, et al., in U.S. Pat. No. 4,361,565 and U.S. Pat. No. 4,411,901; and Temple, in U.S. Pat. No. 4,423,049 disclose and claim compounds of formula 2

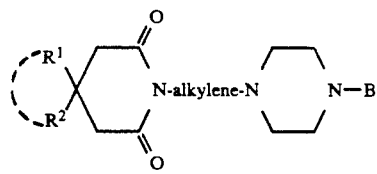

wherein $R^1$ and $R^2$ are alkyl groups or are joined to form $C_4$ or $C_5$ spiro-alkylene bridges and B can be a substituted or unsubstituted pyridine, pyrimidine, or benzisothiazole ring.

B. Succinimide and phthalimide ring examples (formula 3) are described in New, et al., U.S. Pat. No. 4,524,206.

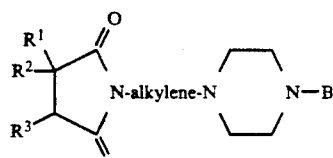

Related psychotropic phthalimide-type compounds where Y is, inter alia, sulfonyl and B is 2-pyrimidinyl were disclosed in EP 129,128-A published Dec. 27, 1984.

C. EP 109,562-A published May 30, 1984, disclosed anti-anxiety and anti-allergy agents wherein X is a fused carbocycle, Y is carbonyl and B is, inter alia, 2-pyrimidinyl.

D. EP 196,132-A published Oct. 1, 1986, disclosed antipsychotic piperidine derivatives of formula 4, as opposed to the piperazine compounds of the instant invention.

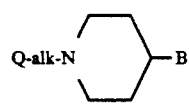

In formula 4, B is benzisothiazole or benzisoxazole and Q is either

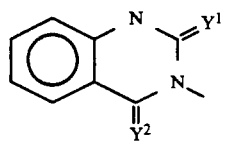

wherein $Y^1$ and $Y^2$ are O or S; or Q is

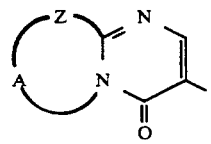

wherein Z is S, methylene or ethylene and A is a $C_2-C_3$ alkanediyl or alkenediyl chain.

E. Also less structurally related to the invention disclosed herein are anxiolytic compounds in which the piperazinylalkyl group is attached to a non-cyclic nitrogen as represented in formula 5 which

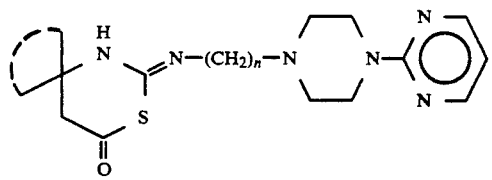

was disclosed in EP 236,931, published Sep. 16, 1987.

F. Other hetero atom containing cyclic imide rings such as morpholinediones, thiazolodinediones, and the like have been described in references represented by Temple, et al., U.S. Pat. No. 4,411,901 (listed hereinabove) and U.S. Pat. No. 4,367,335 and by New, et al., in U.S. Pat. No. 4,619,930.

G. Examples of psychotropic compounds wherein B is a fused heterocyclic ring structure comprising thieno[2,3-c]-pyridine, and furo[3,2-c]pyridine were disclosed and claimed by New, et al., in U.S. Pat. No. 4,677,104.

H. Finally pyrimidinylpiperazinyl derivatives of pyrrolidinones (Y=$CH_2$) have been disclosed by Yevich, et al., in U.S. Pat. No. 4,668,687 as being cognition and memory enhancing agents.

None of the references discloses or suggests the psychotropic piperazine compounds of the instant invention whose structures comprise carboxamide or carboximide moieties incorporated in a fused ring bicyclic heterocycle connected via a butylene chain to the piperazine ring.

SUMMARY OF THE INVENTION

This invention concerns a new series of CNS-active compounds characterized by the following general structural formula I

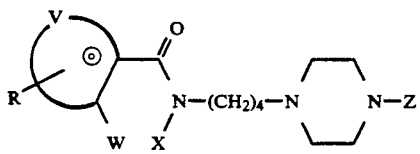

and the pharmaceutically acceptable acid addition salt thereof. In the foregoing formula I, V is a 3- or 4-membered unsaturated chain, containing all carbon atoms when 4-membered and containing an oxgen or sulfur atom when 3-membered. In this way, the chain forms a 5- or 6-membered fused ring. R is hydrogen or $C_{1-4}$ alkyl. W is CH, N, $CH_2$, or a chemical bond; and X is CH, N, $SO_2$, or CO; but W and X cannot be N at the same time. Z is a heteroaromatic ring system selected from pyrimidine, 1,2-benzisolthiazole; thieno[3,2-c]pyridine and furo[3,2-c]pyridine. The dotted line accompanying a full line indicates a single or double bond. The compounds of formula I are psychotropic agents possessing anxiolytic and/or antipsychotic properties.

DETAILED DESCRIPTION OF THE INVENTION

The compounds comprising this invention correspond in structure to formula I, shown and described hereinabove. Contemplated classes of compounds are distinguished by their therapeutic classification. Class 1 is comprised of the compounds of formula I wherein Z is the anxiolytic predisposing pyrimidine ring and Class 2 is comprised of formula I compounds wherein Z is the antipsychotic predisposing 1,2-benzisothiazole, thieno[3,2-c]pyridine, and furo[3,2-c]pyridine rings.

For the compounds of structural formula I, V is either a $C_3$ alkenediyl chain in which one of the carbon atoms can be replaced by an oxygen or sulfur atom or V is a butadienediyl chain. In either case the chain may bear a lower ($C_{1-4}$) alkyl subsitituent. In this way V forms a fused 5- or 6- membered ring giving rise to either structural moiety A or B. In the moieties of formula A and B,

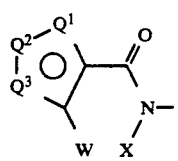

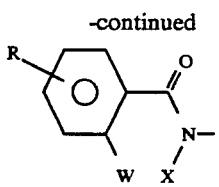

R, W, X and the dotted line are as defined hereinabove. In A, one of $Q^1$, $Q^2$, or $Q_3$ is an oxygen or sulfur atom and the other two Qs are carbon atoms bearing either a hydrogen atom or R. Preferred Formula I compounds are those containing structural moiety A and of these, the more preferred compounds are these in which $Q_1$, or $Q_3$ is oxygen or sulfur. W can be CH, N, $CH_2$ or a chemical bond; and X is CH, N, $SO_2$, or CO; however, both W and X cannot be N at the same time.

Selected compounds exemplary of these hereinabove-described structural variations display useful psychotropic properties including antianxiety and/or antipsychotic action.

It is to be understood that, as used herein, the compounds comprising one aspect of this invention are intended to encompass pharmaceutically acceptable acid addition salts and solvates as well as the base form of these compounds.

Pharmaceutically acceptable acid addition salts of the invention are those in which the anion does not contribute significantly to the toxicity or pharmacological activity of the salt and, as such they are the pharmacological equivalents of the bases of Formula I. These are generally preferred for medical usage. In some instances, these have physical properties which make them more desirable for pharmaceutical formulation such as solubility, lack of hygroscopicity, compressibility with respect to tablet formation and compatibility with other ingredients with which the substances may be used for pharmaceutical purposes. The salts are routinely made by mixture of the Formula I base with the selected acid preferably by contact in solution employing an excess of commonly used inert solvents such as water, ether, benzene, alcohol, e.g. ethanol, ethyl acetate, acetonitrile, and so forth. The salts may also be made by methathesis or treatment with an ion exchange resin under conditions in which the anion of one salt of the substance of the Formula I is replaced by another anion under conditions which allow for separation of the desired species such as by precipitation from solution or extraction into a solvent, or elution or retention on an ion exchange resin. Examples of pharmaceutically acceptable acids for the purposes of salt formation of the substances of Formula I comprise sulfuric, phosphoric, hydrochloric, hydrobromic, hydroiodic, citric, acetic, benzoic, cinnamic, mandelic, nitric, mucic, isethionic, palmitic, heptanoic, and others.

The compounds of Formula I are prepared by means of a three step reaction sequence depicted in Scheme 1.

Scheme 1

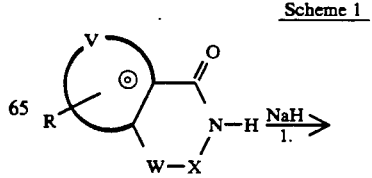

-continued
Scheme 1

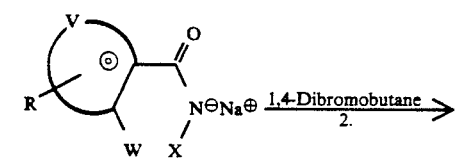

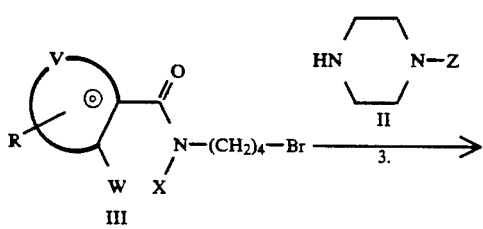

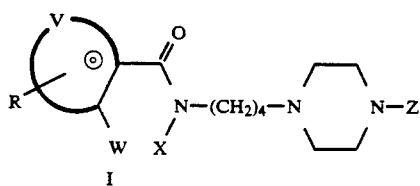

The synthetic steps comprising the processes of Schemes 1-5 are well known to those skilled in organic chemistry and the details are readily available in the chemical literature. These processes may be adapted to variation in order to produce other compounds embraced by this invention but not specifically disclosed. Variations of the methods to produce the same compounds in somewhat different fashion will also be evident to one skilled in the art. Certain examples will be given for specific illustration.

The heteroaryl piperazines of Formula II are described in the aforementioned Wu, et al., Temple, et al. and New, et al. patents and certain references cited therein. These procedures are applicable to the preparation of all the heteroarylpiperazines required as intermediates for the process of scheme 1. Specifically, U.S. Pat. Nos. 4,411,901, 3,717,634, and 4,677,104 are hereby incorporated herein by reference.

The bicyclic amides and imides of Formula IV in which V contains a heteroatom are obtained by synthetic methods requiring differing reaction schemes according to the structure of the desired Formula IV compound. The Formula IV intermediates comprising saccharin, phthalimide, and homophthalimide are available commercially. The other Formula IV intermediate compounds can be obtained by the syntheses, or modifications thereof, which follow.

SYNTHESES OF IV COMPOUNDS

Scheme 2

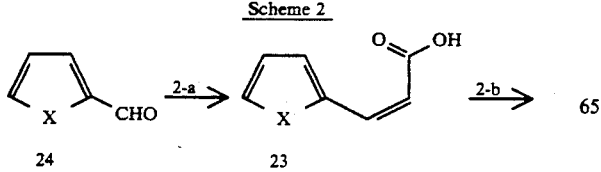

-continued
Scheme 2

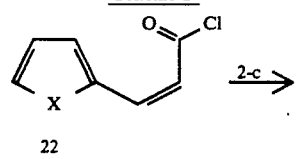

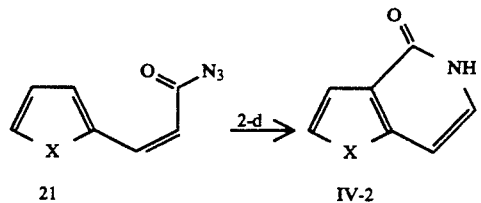

In scheme 2 (above) and the following schemes, X can be sulfur or oxygen. Step 2-a through 2-d involve the following reagents and conditions.

Reagents and Conditions 2-a: $CH_2(CO_2H)_2$, pyridine, piperidine, 90° C.
2-b: $SOCl_2$, $CHCl_3$
2-c: $NaN_3$, water/dioxane
2-d: 235° C., biphenyl (solvent)

Scheme 3

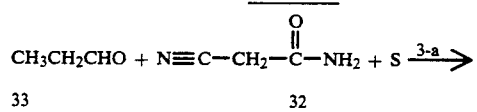

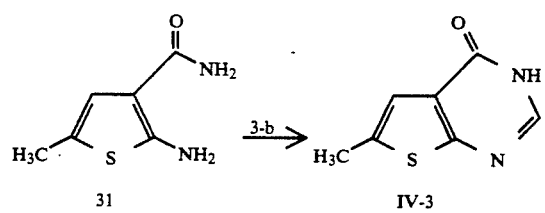

Reagents and Conditions 3-a: $Et_3N$, DMF, 50° C.
3-b: $(EtO)_3CH$, TsOH (10% by wt.)

Scheme 4

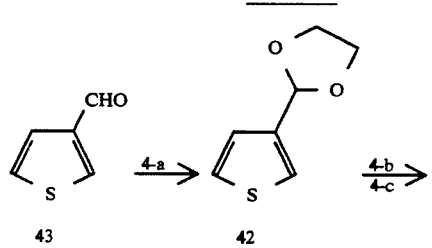

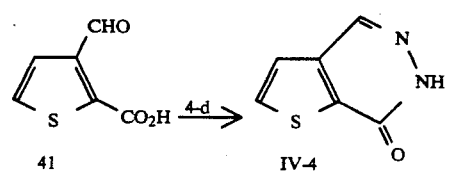

Reagents and Conditions 4-a: HOCH$_2$CH$_2$OH, benzene
4-b: n-BuLi, THF, −78° C.
4-c: 1)CO$_2$; 2)H$^+$
4-d: 5 eq. H$_2$NNH$_2$, MeOH, reflux Scheme 5

HSCH$_2$CO$_2$CH$_3$ + H$_2$C=CH$_2$CO$_2$CH$_3$ $\xrightarrow{5-a}$ 58     57

H$_3$CO$_2$CCH$_2$SCH$_2$CH$_2$CO$_2$CH$_3$ $\xrightarrow{5-b}$

56

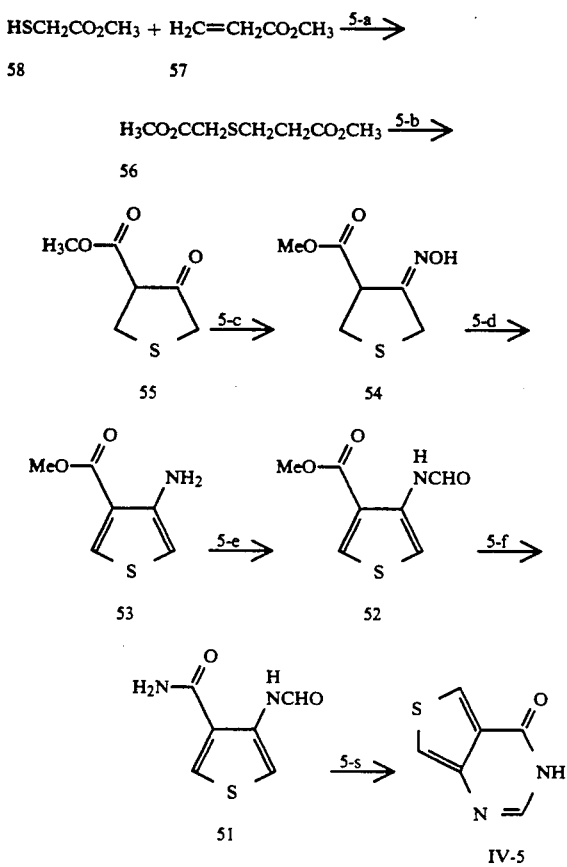

Reagents and Conditions 5-a: piperidine, reflux
5-b: NaOCH$_3$, MeOH, toluene
5-c: H$_2$NOH.HCl, BaCO$_3$, MeOH
5-d: Et$_2$O
5-e: NaOAc, HCO$_2$H
5-f: NH$_3$, EtOH, Sealed vessel
5-g: NaOMe, MeOH, reflux The compounds of the instant invention are useful pharmacological agents with psychotropic properties. In this regard, they exhibit activity at non-toxic doses as anxiolytic and/or antipsychotic agents. Compounds of Formula I wherein Z is a 2-pyrimidinyl moiety are also active in reversing catalepsy. The following in vivo screening tests were utilized as the basis to determine the pharmacological profile of the instant compounds.

| Behavioral Test | Reference |
|---|---|
| Suppression of Conditioned Avoidance Response (CAR) | Albert, Pharmacologist. 4, 152 (1962); Wu, et al., J. Med. Chem., 12, 876–881 (1969) |
| Reversal of trifluoperazine-induced catalepsy | Berkson, Amer. Statist. Assoc., 48: 565–599 (1953) |
| Blockade of apomorphine-induced stereotyped | Janssen, et al., Arzneimittel-Forsch, 17: 841 (1966) |

-continued

| Behavioral Test | Reference |
|---|---|
| behavior | |

The CAR test is generally considered to be a measure of the tranquilizing potential of a drug. It is determined by assaying the drug's ability to attenuate an avoidance response to an electrical shock in trained, fasted rats. The reversal of neuroleptic-induced catalepsy in the rat is considered a desirable component in a compound's biological profile because it may be predictive of a low propensity to induce extrapyramidal side effects in man. For the purpose of this test method, catalepsy is defined as a motionless animal capable of maintaining an abnormal posture for a 30 second time period. The blockade of apomorphine-induced stereotyped behavior in rats may reflect dopamine antagonist activity and is a fairly specific screen for antipsychotic activity.

Formula I compounds, active in the CAR test, but not active in the apomorphine test are classified as anxiolytics on the basis of 5-HT$_{1A}$ binding and Vogel conflict test results. To aid in subclassification of the psychotropic activity and specificity of the instant compounds, state of the art in vitro central nervous system receptor binding methodology is employed. Binding affinity for 5-HT$_{1A}$ receptor sites is suggestive of anxiolytic activity cf: Dourish, et al., Trends in Pharmacological Science, 212–214, (1986); Bockaert, et al., Naunyn-Schmiedeberg's Arch. Pharmacol. 658: 1–5 (1987). Compounds in which Z is pyrimidine exhibited binding at the 5-HT$_{1A}$ site. Selected representative compounds from this subclass also exhibited in vivo activity in a modified Vogel conflict test which is a procedure for testing antianxiety compounds, cf: Vogel, et al., Psychopharmacologia (Berl.) 21, 1–7 (1971).

According to the pharmacological profile established by the aforementioned tests, representative compounds of Formula I have promising tranquilizing potential, either antianxiety and/or antipsychotic activity, in that they are relatively potent in the CAR test, having oral ED$_{50}$ values <100 mg/kg body weight. Concerning prediction of side-effect liability, certain Formula I compounds wherein Z is a pyrimidine ring show activity in the reversal of trifluoperazine-induced catalepsy test by virtue of ED$_{50}$ values being <20 mg/kg, p.o. Activity in this test suggests that the compounds lack the potential for eliciting the unwanted side effects associated with extrapyramidal symptomatology.

The pharmacological profiles established by the above-described tests also served to classify the Formula I compound as either anxiolytic or antipsychotic agents. Activity in the CAR and in blockade of apomorphine-induced stereotyped behavior is predictive of antipsychotic activity. Compounds having ED$_{50}$ values <100 mg/kg body weight in these tests are psychotropics with antipsychotic properties. On these bases the Formula I compounds wherein Z is pyrimidine were classed as psychotropics with anxiolytic properties and a low side-effect potential and the Formula I compounds wherein Z is 1,2-benzisothiazole, thieno-[3,2-c]pyridine and furo[3,2-c]pyridine are psychotropics with antipsychotic properties.

Another aspect of the instant invention provides a method for treating a mammal afflicted with anxiety or psychosis which comprises administering systemically to said mammal a therapeutically effective amount of a compound of Formula I or a pharmaceutically acceptable acid addition salt thereof.

The administration and dosage regimen of compounds of Formula I is considered to be done in the same manner as for the reference compound clozapine, cf: *The Merck Index,* 10th Edition, (1983), page 344, and references therein. Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 10 mg/kg, preferable, 0.1 to 2 mg/kg, when administered parenterally; and from about 1 to about 50 mg/kg, preferably 2 to 30 mg/kg, when administered orally. In some instances, a sufficient therapeutic effect can be obtained at lower doses while in others, larger doses will be required. Systemic administration refers to oral, rectal and parenteral (i.e. intramuscular, intravenous and subcutaneous). Generally, it will be found that when a compound of the present invention is administered orally, a larger quantity of the active agent is required to produce the same effect as a similar quantity given parenterally. In accordance with good clinical practice, it is preferred to administer the instant compounds at a concentration level that will produce effective anxiolytic effects without causing any harmful or untoward side effects.

The compounds of the present invention may be administered for anxiolytic purposes either as individual therapeutic agents or as mixtures with other therapeutic agents. Therapeutically, they are generally given as pharmaceutical compositions comprised of a tranquilizing amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch); and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not be construed as limiting the invention in sphere or scope. In the following examples, used to illustrate the foregoing synthetic processes, temperatures are expressed in degrees Celsius and melting points are uncorrected. The nuclear magnetic resonances (NMR) spectral characteristics refer to chemical shifts ($\delta$) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported as broad singlet (bs), singlet (s), multiplet (m) or doublet (d). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight and are given in Table 3.

The following examples describe in detail the preparation of compounds of formulas I, III and IV. It will be apparent to those skilled in the art that modifications, both of materials and methods, will allow preparation of other compounds disclosed herein. From the foregoing description and the following examples it is believed that one skilled in the art is able to use the invention to the fullest extent.

A. PREPARATION OF FORMULA IV COMPOUNDS

EXAMPLE 1

Furo[3,2-c]pyridin-4(5H)-one, IV-2 (X=O)

A solution of 21 (177 g, 1.1 mol) in CH$_2$Cl$_2$ was added dropwise to mechanically stirred biphenyl (450 g, 2.5 mol) at an internally monitored temperature of approximately 230° C. (the biphenyl may be dissolved in CH$_2$Cl$_2$ to facilitate handling and the CH$_2$Cl$_2$ allowed to evaporate as the solution is being heated to 230° C.). The rate of addition is regulated to maintain an internal reaction temperature above 200° C. and to control the violent CH$_2$Cl$_2$ evaporation as the azide solution is added. After the addition was complete, the reaction solution was allowed to cool to approximately 100° C. and maintained at that temperature while several extractions with boiling water were carried out. The decanted aqueous phases were cooled and the resulting precipitate filtered. Recrystallization from water yielded 49 g (34%) of solid. The NMR was consistent with the assigned structure of IV-2.

EXAMPLE 2

Synthesis of 6-Methyl Thieno [2,3-d]-pyrimidin-4(3H)-one(IV-3)

To a mechanically stirred mixture of 2-cyanoacetamide (140.50 g, 1.67 mol), and sulfur (53.54 g, 1.67 mol) in an ice-cold solution of triethylamine (125 ml) in DMF (300 ml) was added 97.0 g (1.67 mol) of propionaldehyde at a rate such that reaction temperature was maintained below 50° C. The solution was stirred for 24 hrs, concentrated in vacuo, and the residual solid recrystallized from water, affording a brown solid which was collected by vacuum filtration. The solid was triturated with ethanol, the insoluble material removed by filtration and the filtrate concentrated to solid and recrystallized from water to yield 219.8 g (84%) of 2-amino-5-methyl-3-thiophene carboxamide as an orange solid. The NMR was consistent with the assigned structure.

This tri-substituted thiophene 31 (71.0 g, 0.454 mol) was combined with 7.1 g p-toluenesulfonic acid (10% by wt) in 650 ml of triethylorthoformate and heated to 85° C. for 24 hrs. The reaction solution was cooled and 68.2 g (82%) of solid 6-methyl thieno[2,3-d]pyrimidin- 4(3H)-one (IV-3) was collected by vacuum filtration. The NMR was consistent with the assigned structure.

EXAMPLE 3

Synthesis of Thieno[2,3-d]pyridazin-7(6H)-one (IV-4)

The 3-thiophene carboxaldehyde (50.0 g, 0.41 mol) was refluxed in benzene with ethylene glycol (38.11 g, 0.61 mol) in the presence of a catalytic amount of p-toluenesulfonic acid (5 g) with evolved water collected via a Dean-Starke trap. Reflux was continued until water evolution was no longer observed. The reaction solution was cooled, washed with 10% $Na_2CO_3$, and the organic phase isolated, dried ($MgSO_4$), and concentrated to a dark oil. The 3-thiophene ethylene ketal 42 was isolated by vacuum distillation and weighed 38 g (60%). The NMR was consistent with the assigned structure.

The thiophene ketal 42 (51.0 g, 0.33 mol) was dissolved in anhydrous THF and treated with 1.3 equivalents (0.43 mol) of n-butyllithium at −75° C. After 1.5 hrs, carbon dioxide was bubbled into the reaction solution for 45 min at a rate such that reaction temperature was maintained at less than −50° C. The reaction was stirred for 20 min after $CO_2$ addition was complete, allowed to warm to approximately −20° C., and cautiously poured into 1 liter of ice-cold 3N hydrochloric acid. This mixture was extracted twice with ethyl ether, and the extracts combined, dried ($MgSO_4$), and concentrated to a black gum. Recrystallization from water yielded 34 g of 3-carboxyaldehyde-2-thiophene carboxylic acid 41 as a yellow solid (66%). Mass spectrum and NMR results were consistent with the assigned structure. The 2,5-disubstituted acid side product was spectrally indicated as an impurity.

A sample of the acid-aldehyde 41 (34.0 g, 0.22 mol) was combined with 32.7 g (0.66 mol) of hydrazine monohydrate in methanol and refluxed for 24 hrs. The reaction solution was concentrated in vacuo to a solid which was recrystallized from methanol to yield 12.1 g (36%) of thieno[2,3-d]pyridazin-7(6H)-one (IV-4). The NMR was consistent with the assigned structure.

EXAMPLE 4

Synthesis of Thieno [3,4-d]pyrimidin-4(3H)-one (IV-5)

A mixture of compound 51 (2.3 g, 0.014 mol) and sodium methoxide (0.9, 0.017 mol) is stirred in methanol for three days at room temperature. The reaction is filtered, concentrated in vacuo to a solid, and the residue is dissolved in water. Acidification of this solution with acetic acid leads to crystallization of the product. Collection of a second lot from the mother liquor affords a total of 17.5 g (56.8%) of white product. The NMR of this product is consistent with the assigned structure.

B. PREPARATION OF FORMULA III COMPOUNDS

Typical Preparation of Formula III Compounds

EXAMPLE 5

Synthesis of N-(4-Bromobutyl)Thieno-[3,2-c]pyridin-4(5H)-one

A 5.0 g sample (0.033 mol) of thieno[3,2-c]pyridin-4-(5H)-one (IV-2) was added portion-wise to a stirring mixture of 1.58 g (0.066 mol) of sodium hydride in 160 ml of anhydrous DMF. The rate of addition was regulated to maintain a reaction temperature less than 40° C. with a steady evolution of hydrogen gas. The reaction mixture was allowed to equilibrate at room temperature until $H_2$ evolution ceased, then further cooled to 10° C. A sample of 1,4-dibromobutane (35.63 g, 0.165 mol) was added in one portion. The reaction was allowed to return to room temperature and stirred for 1.5 hrs. Concentration in vacuo afforded a gold oil which was partitioned between $CH_2Cl_2$ and water. The organic phase was isolated, dried ($MgSO_4$), and concentrated. The excess dibromobutane was removed by Kugelrohr distillation (49°–55° C., 0.15 mm) and the still pot residue was purified by flash chromatography (1% $EtOH:CHCl_3$) to yield 5.88 (62%) of a gold oil. The NMR was consistent with the assigned structure.

EXAMPLE 6

Synthesis of N-(4-Bromobutyl)-6-Methyl-Thieno[2,3-d]pyrimidin-4(3H)-one

To a stirring mixture of NaH (1.7 g, 0.072 mol) in 150 ml anhydrous DMF at room temperature was added 4.0 g (0.024 mol) of 6-methyl thieno[2,3-d]pyrimidin-4(3H)-one (IV-3) and, after the cessation of gas evolution, 20.7 g (0.96 mol) of 1,4-dibromobutane was added. Reaction was complete after 4 days. The solution was concentrated in vacuo, the residue partitioned between $CH_2Cl_2$ and water, and the organic phase isolated, dried ($MgSO_4$), and filtered. The filtrate was concentrated and excess dibromobutane removed by Kugelrohr distillation. The solid product residue weighed 4.12 g (57%). The NMR was consistent with the assigned structure.

The isolation of these and other bromobutyl intermediate compounds of Formula III rendered products of sufficient purity to be used in the preparation of Formula I compounds without additional purification. The other desired Formula III compounds are easily obtained by modification of these foregoing examples in a manner familiar to one skilled in the pertinent art.

C. PREPARATION OF FORMULA I COMPOUNDS

The heteroarylpiperazines of Formula II are prepared by the methods detailed in U.S. Pat. Nos. 3,717,634; 4,411,901; and 4,677,104; all of which are hereby incorporated by reference into the disclosure contained in this specification. These Formula II compounds are required in the synthesis of the Formula I CNS agents as shown in the following.

Typical Preparation of Formula I Compounds

EXAMPLE 7

Synthesis of 5-[4-(2-Pyrimidinyl)-1-piperazine]butyl]thieno [3,2-c]pyridin-4(5H)-one Dihydrochloride A mixture of 2.0 g (0.0069 mol) of N-(4-bromobutyl)-thienopyridinone (Example 5), 1.14 g (0.0069 mol) of 1-(2-pyrimidinyl)pyrimidine, and 1.90 g (0.013 mol) of potassium carbonate was refluxed for 24 hrs in acetonitrile. The reaction solution was concentrated and the residue flash chromatographed in 8% ethanol-chloroform to yield an oil weighing 1.1 g (38%). Treatment with two equivalents of ethanolic hydrochloric acid yielded a white solid which was recrystallized from acetonitrile to give 1.2 g (92%) of desired product melting 241°–247° C.

IR (KBr) 3450, 2450, 1660, 1645, 1625, 1610, 1590, 1555, 1440, 1350, 760, 700 cm$^{-1}$;

$^1$H NMR (Me$_2$SO-d$_6$) δ—1.78 (m, 4H), 3.05 (m, 2H), 3.14 (m, 2H), 3.54 (m, 4H), 4.03 (t, J=7.0 Hz, 2H), 4.72 (d, J=14.8 Hz, 2H) 6.55 (br.s, 1H), 6.80 (t, J=4.8 Hz, 1H), 6.95 (d, J=7.2 Hz, 1H), 7.51 (d, J=5.2 Hz, 1H), 7.64 (m, 2H), 8.47 (d, J=4.8 Hz, 2H), 11.68 (br.s, 1H) ppm;

$^{13}$C NMR (Me$_2$SO-d$_6$) δ—20.1, 26.1, 40.2, 47.0, 50.1, 54.8, 101.2, 111.0, 124.3, 125.5, 130.0, 133.3, 147.0, 157.9, (2 peaks), 159.9 ppm.

EXAMPLE 8

Synthesis of 6-Methyl-3-[4-[4-(2-pyrimidinyl)-1-piperazinyl]butyl]-thieno[2,3-d]pyrimidin-4(3H)-one A mixture of 2.5 g (0.0083 mol) of N-(bromobutyl)-6-methyl-thienopyrimidinone (Example 6), 1.36 g (0.00083 mol) of 1-(2-pyrimidinyl)piperazine, and 2.64 g (0.0249 mol) of sodium carbonate was refluxed in n-butanol for 7 hrs. The reaction mixture was filtered, concentrated, and the residue flash chromatographed (9% ethanol-chloroform) to yield 1.6 g (50%) of yellow solid, which was recrystallized from ethanol to give product melting 114°-115° C.

IR (KBr) 3440, 2940, 2830, 1670, 1595, 1550, 1500, 1360, 1260, 980, 770, cm$^{-1}$;

$^1$H NMR (CDCl$_3$) δ1.60 (m, 2H), 1.85 (m, 2H), 2.40 (t, J=7.3 Hz, 2H), 2.47 (m, 4H), 2.52 (s, 3H), 3.81 (m, 4H), 4.04 (t, J=7.2 Hz, 2H), 6.46 (t, J=4.7 Hz, 1H), 7.10 (s, 1H), 7.97 (s, 1H), 8.28 (d, J=4.7 Hz, 2H) ppm;

$^{13}$C NMR (CDCl$_3$δ—16.0, 23.9, 27.6, 43.6, 46.5, 53.1, 57.9, 109.7, 119.3, 124.9, 138.4, 145.6, 156.9, 157.5, 161.5, 162.5 ppm.

EXAMPLE 9

Synthesis of 5-[4-(1,2-Benzisothiazol-3-yl)-1-piperazinyl]butyl]-thieno[3,2-c]-pyridin-4(5H)-one Hydrochloride Hydrate A mixture of N-(4-bromobutyl)thienopyridinone (Example 5, 2.0 g, 0.0069 mol), 3-(1-piperazinyl)-1,2-benzisothiazole hydrochloride (1.79 g, 0.0069 mol), and potassium carbonate (2.90 g, 0.021 mol) was refluxed in acetonitrile for 24 hrs. The reaction mixture was filtered, concentrated and the residue flash chromatographed (10% ethanol-chloroform) to yield 2.05 g (69%) of an oil. Treatment with an equivalent of ethanolic HCl gave a solid product which was recrystallized from a mixture of ethanol and isopropanol (1:2) to provide 2.0 g of product melting 238°-241° C.

IR (KBr) 3450, 2940, 2820, 1670, 1570, 1560, 1490, 1380, 1250, 775, 740, cm$^{-1}$;

$^1$H NMR (Me$_2$SO-d$_6$) δ—1.49 (m, 2H), 1.74 (m, 2H), 2.36 (m, 2H), 2.51 (m, 4H), 3.43 (m, 4H), 4.02 (m, 2H), 7.12 (s, 1H), 7.43 (m, 1H), 7.55 (m, 1H), 8.04 (m, 2H), 8.41 (s, 1H), ppm;

$^{13}$C NMR (Me$_2$SO-d$_6$) δ15.5, 23.2, 26.6, 45.6, 49.6, 52.4, 57.2, 119.1, 120.9, 124.0, 124.2, 127.2, 127.7, 137.7, 147.4, 151.9, 156.2, 162.0, 163.4 ppm.

Compound preparation data for these and other Formula I compounds, which are prepared in a manner similar to the above procedures, is shown in Tables 1 and 2. The modification of materials to be used in these procedures would be known to one skilled in the art.

TABLE 1

Formula I Compounds with Z as Pyrimidine

| Ex. No. | Structure | Formula | MP °C. | Recrys. Solvent |
|---|---|---|---|---|
| 7 | 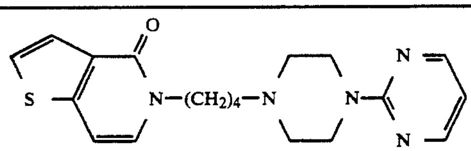 | C$_{15}$H$_{23}$N$_5$OS.2 HCl | 241–247 | CH$_3$CN |
| 10 | 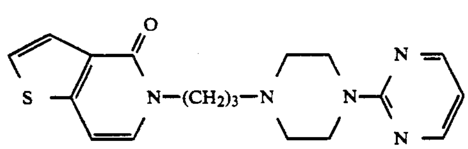 | C$_{18}$H$_{21}$N$_5$OS.2 HCl.1.1 H$_2$O | 204 | CH$_3$CN/EtOH |
| 8 | 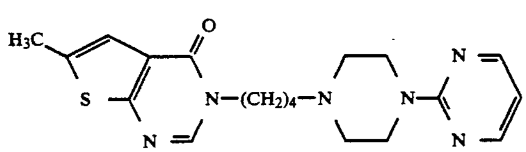 | C$_{19}$H$_{24}$N$_6$OS | 114–115 | EtOH |
| 11 | 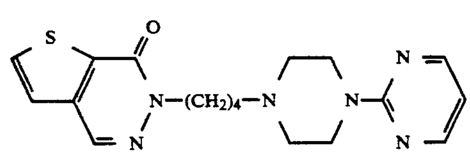 | C$_{18}$H$_{22}$N$_6$OS | 101–102 | CH$_3$CN |
| 12 | 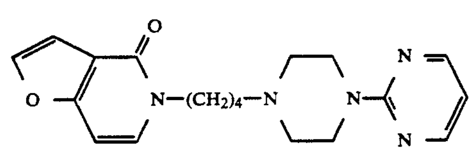 | C$_{19}$H$_{23}$N$_5$O$_2$.2 HCl.0.1 H$_2$O | 224–226 | EtOH |

TABLE 1-continued

Formula I Compounds with Z as Pyrimidine

| Ex. No. | Structure | Formula | MP °C. | Recrys. Solvent |
|---|---|---|---|---|
| 13 | 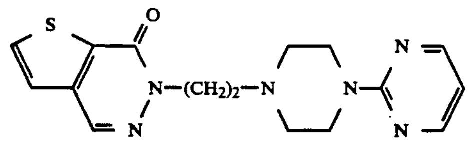 | $C_{16}H_{18}N_6OS$ | 133–134 | EtOAc |
| 14 | 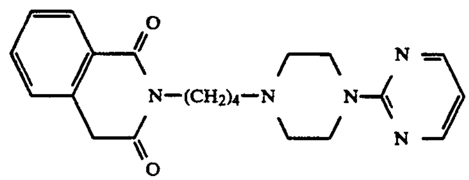 | $C_{21}H_{25}N_5O_2$ | 89.5–90.5 | IPrOH |

TABLE 2

Formula I Compounds with Z as Bicyclic Heterocycles

| Ex. No. | Structure | Formula | MP °C. | Recrys. Solvent |
|---|---|---|---|---|
| 15 | 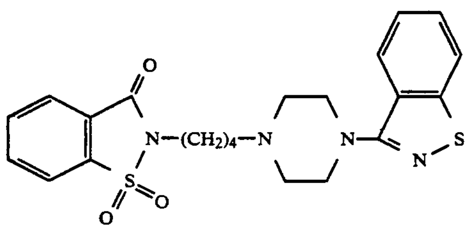 | $C_{22}H_{24}N_4O_3S_2 \cdot HCl$ | 220–222 | $CH_3CN$/EtOH |
| 9 | 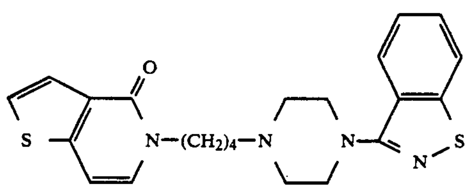 | $C_{22}H_{24}N_4OS_2 \cdot HCl \cdot 0.4\ H_2O$ | 238–241 | EtOH/IPrOH |
| 16 | 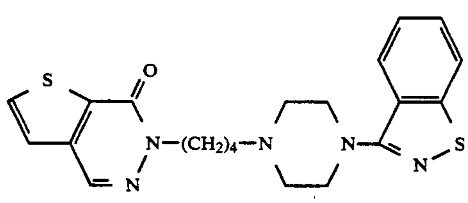 | $C_{21}H_{23}N_5OS_2$ | 135–136 | MeOH |
| 17 | 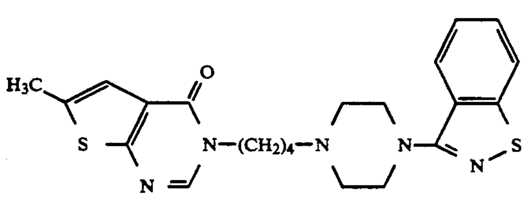 | $C_{22}H_{25}N_5OS_2$ | 133–135 | $CH_3CN$ |
| 18 | 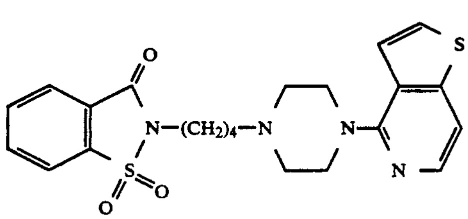 | $C_{22}H_{24}N_4O_3S_2 \cdot HCl$ | 229–230 dec. | EtOH |

TABLE 2-continued

Formula I Compounds with Z as Bicyclic Heterocycles

| Ex. No. | Structure | Formula | MP °C. | Recrys. Solvent |
|---|---|---|---|---|
| 19 | ![structure 19] | $C_{23}H_{24}N_4O_2S \cdot HCl \cdot 0.05\ H_2O$ | 226–227 | EtOH |
| 20 | ![structure 20] | $C_{23}H_{24}N_4O_3 \cdot HCl \cdot C_2H_6O$ | 219–221 | EtOH/CHCl$_3$ |

TABLE 3

Elemental Analysis Data For Formula I Compounds

| Ex. No. | Theoretical | Found |
|---|---|---|
| 7 | 51.58, 5.70, 15.83 | 51.29, 5.71, 15.85 |
| 8 | 59.35, 6.29, 21.86 | 59.25, 6.31, 21.67 |
| 9 | 56.43, 5.55, 11.97 | 56.29, 5.47, 11.79 |
| 10 | 48.24, 5.67, 15.63 | 48.05, 5.49, 15.50 |
| 11 | 58.36, 5.99, 22.68 | 58.59, 6.06, 22.77 |
| 12 | 53.53, 5.91, 16.43 | 53.26, 5.97, 16.22; 0.49 |
| 13 | 56.12, 5.30, 24.54 | 55.92, 5.35, 24.16 |
| 14 | 66.47, 6.64, 18.46 | 66.21, 6.73, 18.07 |
| 15 | 53.59, 5.11, 11.36 | 53.26, 5.27, 11.53 |
| 16 | 59.27, 5.45, 16.46 | 59.06, 5.52, 16.31 |
| 17 | 60.11, 5.73, 15.93 | 60.14, 5.83, 16.02 |
| 18 | 53.59, 5.11, 11.36 | 53.47, 5.24, 11.67 |
| 19 | 60.33, 5.53, 12.24; 0.20 | 59.91, 5.57, 12.01; 0.15 |
| 20 | 61.65, 6.42, 11.50 | 61.34, 6.30, 11.37 |

What is claimed is:

1. A compound of Formula I and its pharmaceutically acceptable acid addition salts thereof

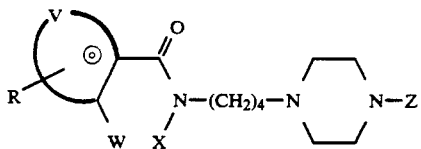

wherein

V is

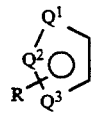

(A)

in which one of $Q^1$, $Q^2$ or $Q^3$ is an oxygen or sulfur atom and the other two Qs are carbon atoms bearing either a hydrogen atom or R which is a $C_{1-4}$ alkyl group;

W is N;

X is CH;

the dotted line accompanying the full line is a double bond; and

Z is a heteroaromatic ring system selected from pyrimidine, 1,2-benzisothiazole, thieno[3,2-c]pyridine, and furo[3,2-c]pyridine.

2. The compound of claim 1 wherein Z is pyrimidine.

3. The compound of claim 1 wherein Z is selected from 1,2-benzisothiazole, thieno[3,2-c]pyridine and furo[3,2-c]pyridine.

4. The compound of claim 1, 6-Methyl-3-[4-[4-(2-pyrimidinyl)-1-piperazinyl]butyl]thieno[2,3-d]pyrimidin-4(3H)-one.

5. The compound of claim 1, 6-Methyl-3-[3-[4-[4-(1,2-benzisothiazol-3-yl)-1-piperazinyl]butyl]thieno[2,3-d]pyrimidin-4(3H)-one.

* * * * *

UNITED STATES PATENT AND TRADEMARK OFFICE
CERTIFICATE OF CORRECTION

PATENT NO. : 5,206,365
DATED : April 27, 1993
INVENTOR(S) : James S. New, William L. Christopher It is certified that error appears in the above-indentified patent and that said Letters Patent is hereby corrected as shown below:

Abstract and column 17, line 45 and in the abstract the structure should be:

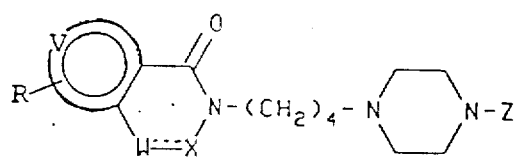

I column 18, lines 40, 41, 44 and 45
"/3,2-c/pyridine"...." should be [3,2-c]pyridine.......

column 18, lines 47 and 50
"/2,3-d/pyrimidin....." should be [2,3-d]pyrimidin.....

Signed and Sealed this

Eighth Day of February, 199

Attest:

BRUCE LEHMAN

Attesting Officer    Commissioner of Patents and Trademarks